US009616216B2

United States Patent
Dulong et al.

(10) Patent No.: US 9,616,216 B2
(45) Date of Patent: Apr. 11, 2017

(54) RELEASABLE BLOCKING SYSTEM OF A CATHETER

(71) Applicant: Vygon, Ecouen (FR)

(72) Inventors: Claire Dulong, Rivecourt (FR);
Jean-Luc Carrez, Ecouen (FR);
Pierrick Guyomarc'h, Ermont (FR);
Jean-Louis Coussegal, Beauchamp (FR)

(73) Assignee: Vygon (FR)

( * ) Notice: Subject to any disclaimer, the term of this patent is extended or adjusted under 35 U.S.C. 154(b) by 711 days.

(21) Appl. No.: 14/023,836

(22) Filed: Sep. 11, 2013

(65) Prior Publication Data
US 2014/0074046 A1    Mar. 13, 2014

(30) Foreign Application Priority Data

Sep. 11, 2012   (FR) ..................... 12 58528

(51) Int. Cl.
*A61M 39/28*   (2006.01)
*A61M 39/12*   (2006.01)
(Continued)

(52) U.S. Cl.
CPC .......... *A61M 39/284* (2013.01); *A61M 39/12* (2013.01); *A61M 2039/2486* (2013.01); *A61M 2039/268* (2013.01)

(58) Field of Classification Search
CPC .... A61M 39/12; A61M 39/28; A61M 39/284; A61M 39/285; A61M 39/286; A61M 39/288
(Continued)

(56) References Cited

U.S. PATENT DOCUMENTS 3,856,010 A    12/1974  Moorehead et al.
6,234,448 B1 *  5/2001  Porat ................. A61M 39/284
                                                        251/10
(Continued)

FOREIGN PATENT DOCUMENTS

WO         0003165 A2    1/2000
WO      2010028021 A1    3/2010
WO      2011106077 A2    9/2011

OTHER PUBLICATIONS

French Preliminary Search Report for Application No. FR 1258528 dated Jul. 10, 2013.

*Primary Examiner* — Rebecca E Eisenberg
(74) *Attorney, Agent, or Firm* — Lerner, David, Littenberg, Krumholz & Mentlik, LLP

(57) ABSTRACT

The invention relates to a releasable blocking system (1) of a catheter (4), comprising a base (2) adapted to receive a catheter (4), and a shell (3), mounted in rotation on the base (2) between an open position, in which the shell (3) is away from the base (2), and a closed position, in which the shell (3)is hooked on the base (2) and blocks the catheter (4) in position, in which:
the system comprises an actuator (25) provided with a guide aperture (251), mobile in a housing (20) between a rest position and a blocking position, the actuator (25) comprising a first drive element (255),
the shell (3)comprises a second drive element (33), adapted to cooperate with the first drive element (255) when the shell (3) is shifted from its open position to its closed position, and shift the actuator (25) to its blocking position.

18 Claims, 8 Drawing Sheets

(51) Int. Cl.
*A61M 39/24* (2006.01)
*A61M 39/26* (2006.01)

(58) Field of Classification Search
USPC ...... 604/93.01, 164.01, 165.01, 165.02, 246, 604/250
See application file for complete search history.

(56) References Cited

U.S. PATENT DOCUMENTS

| | | |
|---|---|---|
| 2003/0225379 A1 | 12/2003 | Schaffer et al. |
| 2006/0116660 A1* | 6/2006 | Cawley ............ A61M 25/0097 604/533 |
| 2010/0274174 A1 | 10/2010 | Swisher |
| 2011/0264105 A1* | 10/2011 | Barthold ............ A61B 17/3462 606/108 |

* cited by examiner

RELEASABLE BLOCKING SYSTEM OF A CATHETER

CROSS-REFERENCE TO RELATED APPLICATIONS

The present application claims the benefit of application Ser. No. FR1258528, filed on Sep. 11, 2012, the disclosure of which is hereby incorporated herein by reference.

FIELD OF THE INVENTION

The invention relates in general to a releasable blocking system adapted to put a medical device and a catheter in fluidic communication.

BACKGROUND OF THE INVENTION

Catheters, and in particular catheters for locoregional anaesthesia, are small in diameter, most often of the order of 0.43*0.80 mm, 0.50*0.90 mm or even 0.50*1.00 mm, and made of relatively elastic material especially to avoid the plication problems. Given the small dimension of these catheters, they are therefore difficult to block ergonomically in a base. But this is necessary if the aim is to connect the catheter to a medical device, such as a filter within the scope of locoregional anaesthesia.

It has therefore been proposed to use a base, comprising a body adapted for housing a sleeve made of elastomer material, having an internal aperture designed to receive the catheter, and able to be compressed by means of a nut by screwing. The radial compression of the sleeve by the nut in fact holds the catheter in position in the base. This type of base is for example illustrated in patent application FR 2 896 698 in the name of the applicant.

In use, the applicant noted that the nut compressing the sleeve risked being lost, especially when the latter is unscrewed to enable introduction of the catheter in the compressible sleeve. It is no longer possible to use the base, or at least the lost piece should be replaced. Also, during screwing, the nut risks pulling along the compressible sleeve in rotation by twisting it on itself, such that once the catheter is blocked, the sleeve risks resuming its initial form by pulling along the nut in turn, releasing the stress applied to the catheter, which can be harmful to proper mechanical behaviour of the catheter in the base.

Also, when the base is fixed to a medical device such as a filter and the latter must be changed or simply pulled out, unscrewing the medical device from the nozzle (generally of standard Luer or Luer Lock type) of the base can cause the unscrewing of the nut, to the extent where it is necessary to hold the base by the nozzle during unscrewing of the medical device.

The applicant has also noted that it was difficult to determine if the catheter were correctly held in the base, to the extent where nothing confirms that the nut is sufficiently screwed on the compressible sleeve or the catheter is correctly inserted in the base. Also, such screwing today is not considered ergonomic.

It has also been proposed to utilise a base comprising a relatively thin tubular sleeve, having a central aperture whereof the diameter is substantially equal to that of the catheter to be blocked, and designed to be compressed radially.

For example, document WO 2011/106077 proposes a system comprising a base, comprising a deformable thin sleeve adapted to receive a catheter and a shell fitted with internal grooves. The shell is mounted in rotation on the base and adapted to radially deform the sleeve by means of the internal grooves when it is closed on the base so as to locally reduce the internal diameter of the sleeve and block the catheter in position.

Document US 2003/0225379 describes a valve adapted to detachably receive a catheter and, when necessary, prevent the passage of fluids in this catheter. For this purpose, the valve comprises a base adapted to receive the catheter, and a shell, mounted in translation on the base between an open position, in which the shell is away from the base, and a closed position, in which the shell is hooked on the base and blocks the catheter in position. The base defines a housing enclosing a sleeve provided with a blocking aperture adapted to receive the catheter. The system also comprises an actuator mobile in translation in the housing between a rest position and a blocking position in which the actuator applies a transversal force to the sleeve to deform it locally. In this accurate blocking position, the actuator also deforms the catheter to prevent the passage of fluids.

BRIEF SUMMARY OF THE INVENTION

An aim of the invention is to propose a releasable blocking system of a catheter in a base, which is ergonomic, easy to use and efficacious, without needing excessive force from an operator.

Optionally, another objective is to ensure an operator that the catheter is properly blocked by the system, avoiding pieces easily being misplaced and the system staying locked, except for intervention by an operator.

For this purpose, the invention proposes a releasable blocking system of a catheter, especially a catheter for locoregional anaesthesia, comprising a base adapted to receive a catheter, and a shell, rotatably mounted on the base between an open position, in which the shell is away from the base, and a closed position, in which the shell is hooked on the base and blocks the catheter in position, the system being characterised in that:
- the base defines a housing having a principal direction according to a longitudinal axis, said housing enclosing a sleeve provided with a blocking aperture extending along the longitudinal axis and adapted to abut against a distal wall of the housing,
- the system comprises an actuator provided with a guide aperture extending along the longitudinal axis and mobile in translation along this longitudinal axis in the housing between a rest position and a blocking position in which the actuator applies an axial force to the sleeve to deform it, the actuator comprising a first drive element,
- the blocking aperture and the guide aperture are adapted to receive a catheter, and
- the shell comprises a second drive element, adapted to cooperate with the first drive element of the actuator when the shell is shifted from its open position to its closed position, and shift the actuator along the longitudinal axis to its blocking position.

Some optional, though non-limiting, characteristics of a releasable blocking system according to the invention are the following:
  the housing comprises:
  a blocking chamber,
  a ring extending in the extension of the blocking chamber along the longitudinal axis, and
  a channel, extending between the blocking chamber and the ring, along the longitudinal axis, an external diameter of the distal part of the actuator is at most equal to the internal diameter of the ring, an internal diameter of the blocking aperture of the sleeve is substantially equal to the external diameter of the catheter, the housing comprises an opening extending opposite the first drive element of the actuator, the second drive element of the shell being positioned so as to cooperate with the first drive element through said opening of the housing, the first drive element has a return ramp extending to the exterior from the distal part of the actuator, and the second drive element comprises a projecting part extending from the shell, arranged so as to come into contact with said return ramp when the shell is brought to its closed position, the element is substantially annular in form, and the return ramp is oriented obliquely relative to a plane normal to the longitudinal direction, the element also comprises a proximal locking wall extending from the return ramp in a plane substantially perpendicular to the longitudinal direction, adapted to come into contact with a distal wall of the projection when the shell in its closed position, the distal part also comprises a protuberance extending radially from said distal part, adapted to prevent the actuator from coming out of the housing, the actuator and the housing are fitted with one or more rectilinear grooves and throats, extending radially from the actuator, adapted to prevent the rotation of the actuator in the base, the base also comprises a connecting element to a medical device, said connecting element being in fluidic communication with the housing, the system also comprises a transparent viewing chamber extending between the housing and the connecting element, adapted to receive a free end of the catheter, the shell comprises hooking means on the base, the hooking means comprise at least one hook engaged in an orifice in the base so as to be released to open the releasable blocking system, and the hooking means comprise hooks, fixed on the shell and adapted to cooperate by snap-locking with tabs extending from the base, said tabs being elastically deformable so as to allow an operator to release the hooks by simple pressure.

BRIEF DESCRIPTION OF THE DRAWINGS

Other characteristics, aims and advantages of the present invention will emerge from the following detailed description, given in reference to the attached figures given by way of non-limiting examples and in which:

FIG. 8c is a view in perspective of the shell of the blocking system of FIG. 8a, and FIG. 8d is a plan view of the base of the blocking system of FIG. 8a.

DETAILED DESCRIPTION

Figure 1:
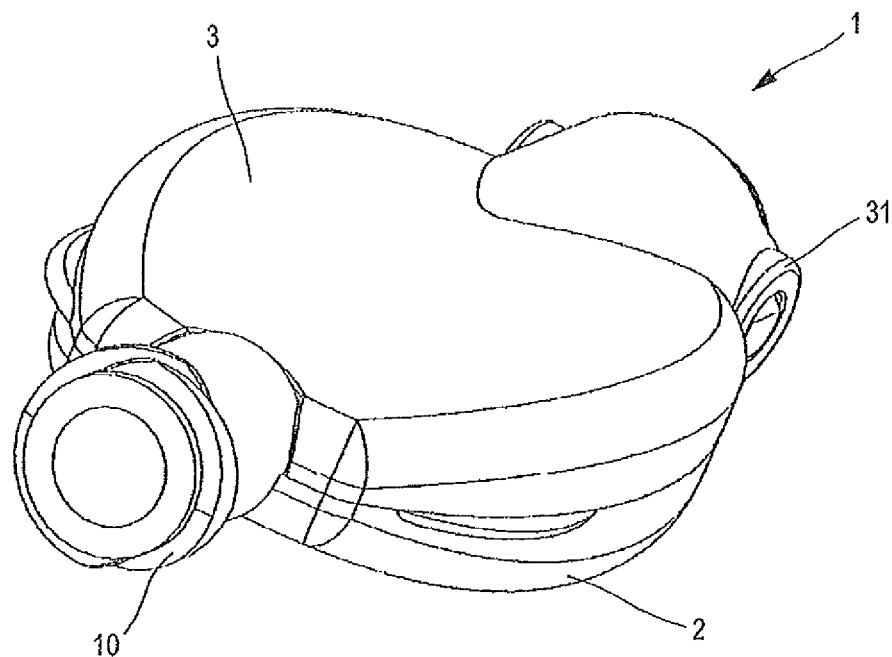
FIG. 1 is a perspective view of an embodiment of a releasable blocking system according to the invention, in closed position.
Figure 2:
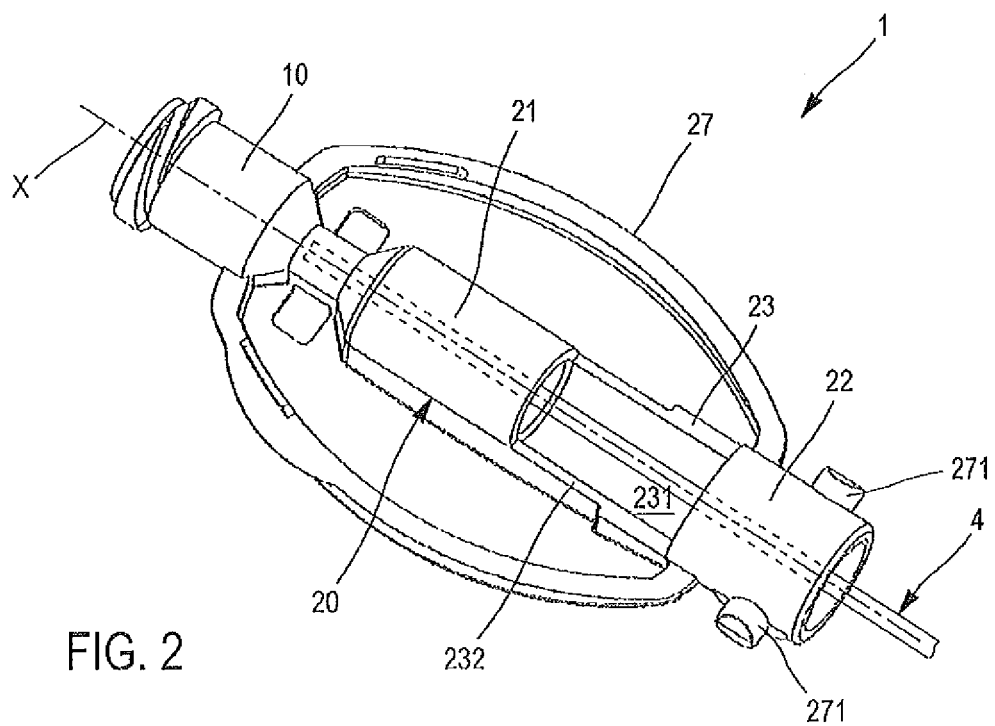
FIG. 2 is a plan view of an embodiment of a base of a releasable blocking system according to the invention, in which the sleeve and the actuator are not shown.
Figure 3A:
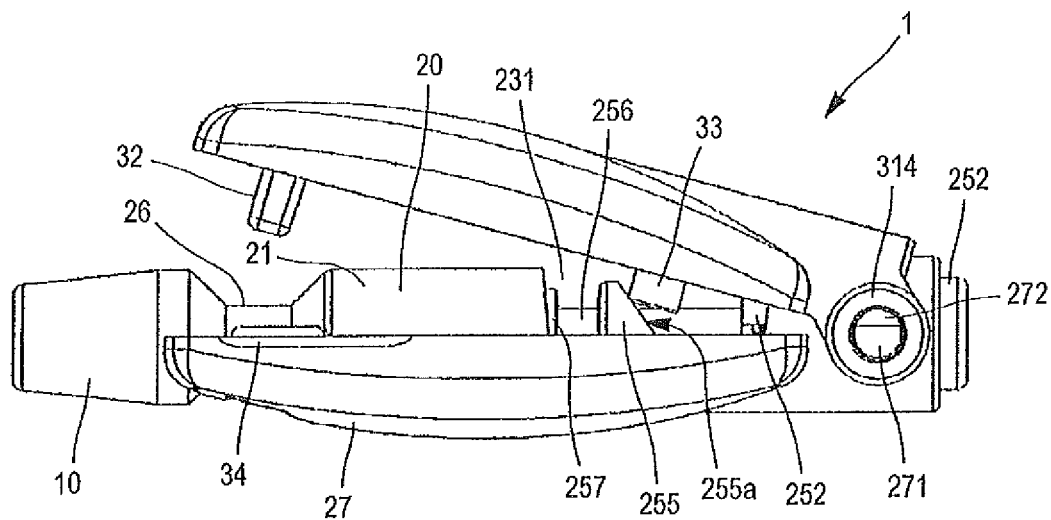
FIG. 3a is a side elevation of the releasable blocking system of FIG. 1, the system being open.
Figure 3B:
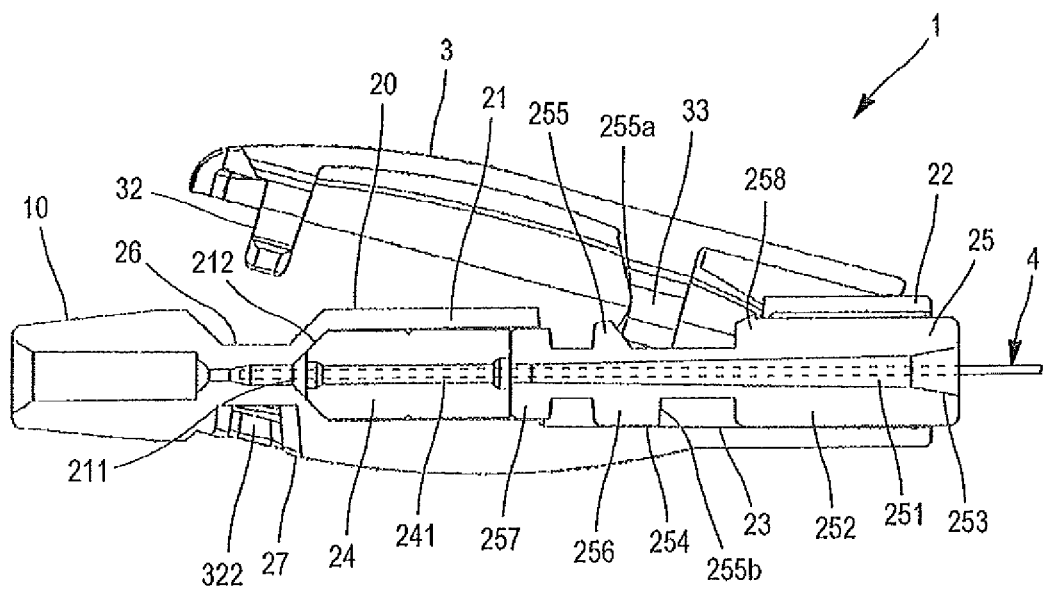
FIG. 3b is a view in transversal section of the releasable blocking system of FIG. 3a, FIG. 3c is a view in transversal section of the releasable blocking system of FIG. 3a, the system being closed.
Figure 3C:
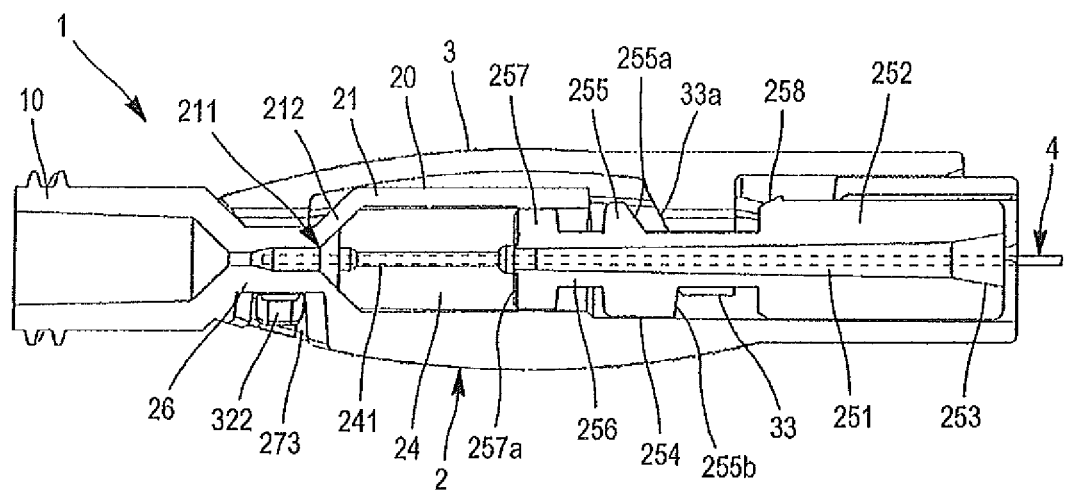
FIG. 3d is a side elevation in detail of an embodiment of the blocking means when the blocking system is en closed position.
Figure 3D:
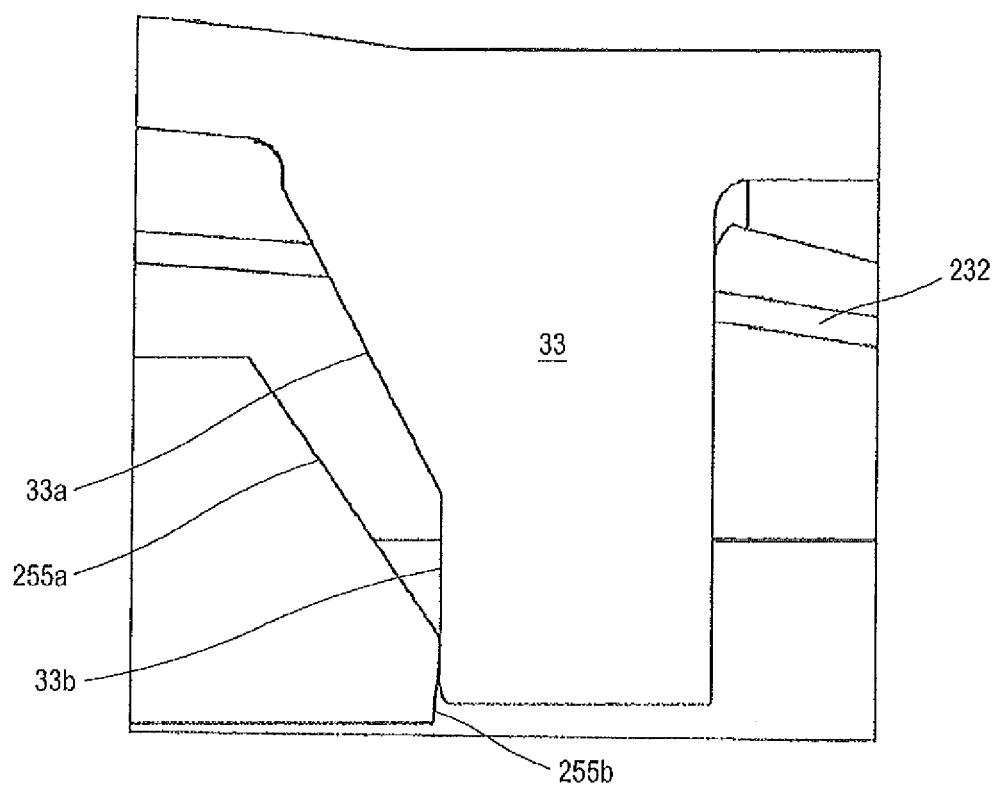
Figure 4:
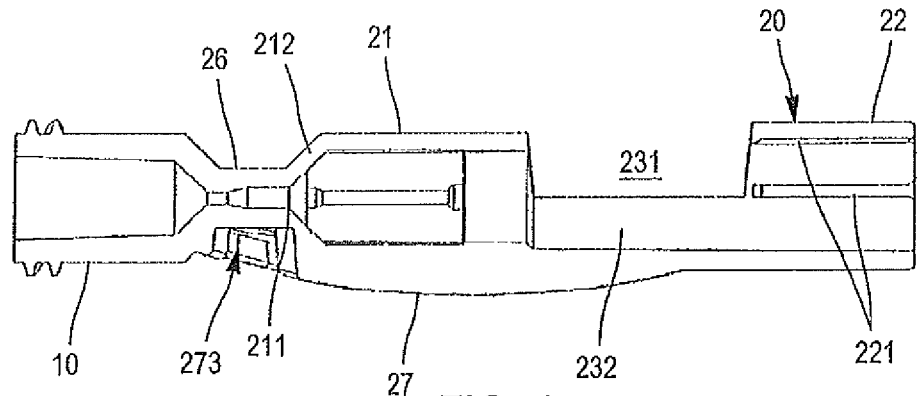
FIG. 4 is a sectional view of an embodiment of the base of FIG. 2.
Figure 5A:
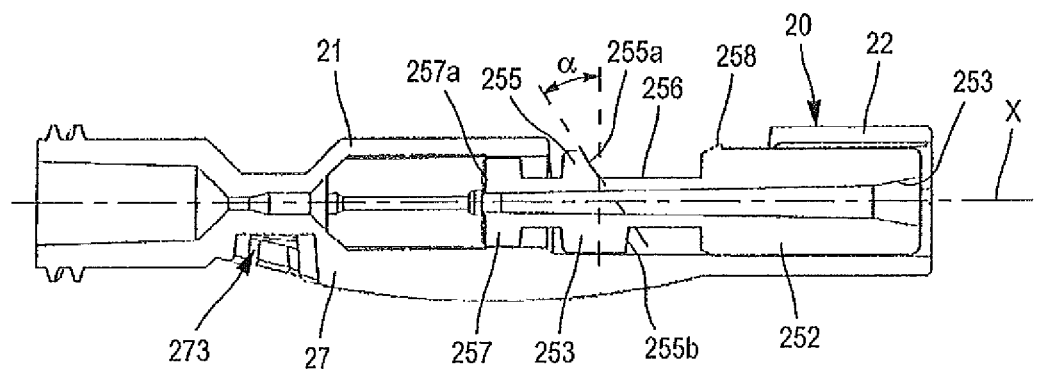
FIG. 5a is a view in transversal section according to a plane passing through the longitudinal axis X of the base of FIG. 2, in which embodiments of a sleeve and an actuator are shown.
Figure 5C:
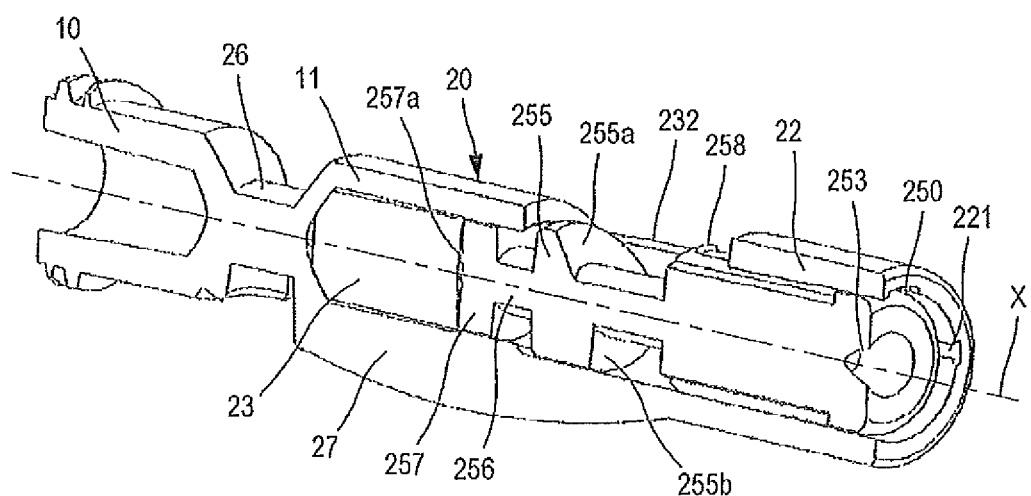
FIG. 5b is a view in perspective of the base fitted with the sleeve and the actuator of FIG. 5a, FIG. 5c is a view in transversal section in perspective, according to a plane parallel to the plane of FIG. 5a, the base fitted with the sleeve and the actuator of FIG. 5a, FIG. 6 is a bottom plan view of an embodiment of a releasable blocking system according to the invention.
Figure 5B:
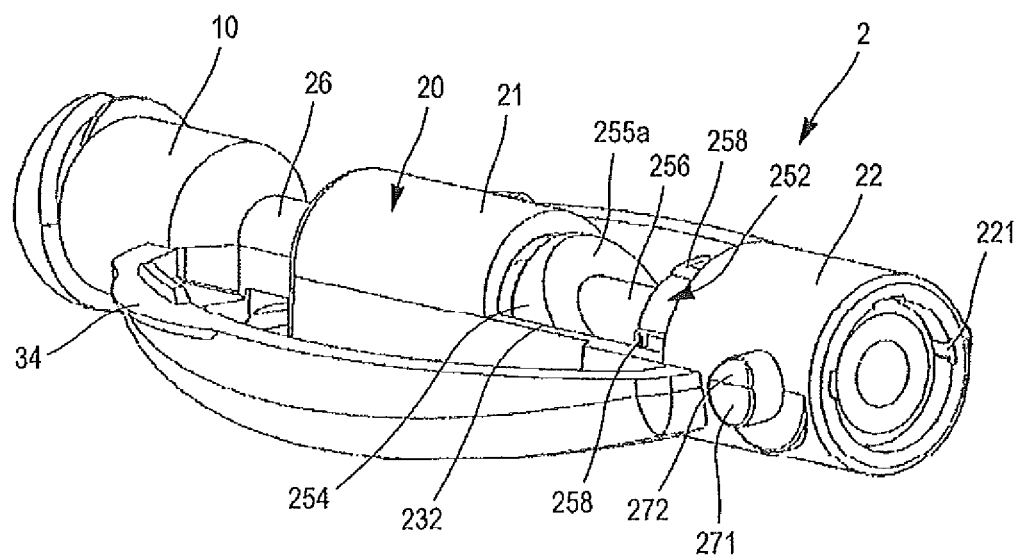

A releasable blocking system 1 of a catheter according to the invention will now be described in reference to the attached figures.

The system comprises a base 2, adapted to receive a catheter 4, for example a catheter for locoregional anaesthesia, and a shell 3, which can be fixed on the base 2 so as to block the latter in position detachably. The blocking system 1 also comprises a connecting element 10 with a medical device, for example a filter, to put the catheter 4 in fluidic communication (once the latter is inserted and blocked in the system) with the medical device. In conventional terms this can be a nozzle of Luer or Luer Lock type, male or female.

The shell 3 comprises connecting means 31 on the base 2, preferably by ball joint link, hooking means 32 on the base 2, and a drive element 33.

The base 2 comprises a housing 20, having a principal direction according to a longitudinal axis X, said housing 20 comprising:

an opening 231 arranged opposite the shell 3, a sleeve 24, housed in the housing 20, an actuator 25, mobile in translation in the housing 20 between a blocking position, in which the actuator 25 applies an axial force to the sleeve 24 to deform it, and a rest position, in which the actuator 25 applies no substantial force to the sleeve 24, the actuator 25 comprising a drive element 255 adapted to cooperate with the drive element 33 of the shell 3, arranged at least partially opposite the opening of the housing 20, and an aperture 251, 241 adapted to receive a catheter 4, passing through the actuator 25 and the sleeve, and extending along the longitudinal axis X.

Hereinbelow, « proximal » shall designate a part (for example an end) which is located near an operator, while « distal » shall designate a part which is away from the operator.

For example, the housing 20 comprises:

a blocking chamber 21, a ring 22, extending in the extension of the blocking chamber 21, and a channel 23, extending between the blocking chamber 21 and the ring 22, forming an opening 23.

The blocking chamber 21, the channel 23 and the ring extend successively according to the longitudinal axis X, along the principal direction of the housing 20. They can be positioned relative to each other by connection to a base 27. As a variant, the housing 20 can be monobloc, than fixed on the base 27. According to yet another variant, the housing 20 and the base 27 are monobloc.

The sleeve 24 is housed in the blocking chamber 21, while the actuator 25 is housed at least partially in the channel 23 and the ring 22.

The shell 3 is preferably articulated on the base 2 by means of a pivot link. For this, the base 27 can comprise for example two pins 271, adapted to cooperate with two lugs 311 comprising complementary orifices extending from the shell 3, at the level of an end of the system 1. The pins 271 can have a chamfer 272 for easier installation of the lugs 311 of the shell 3.

The blocking chamber 21 can for example have an substantially tubular form, having a proximal opening terminating in the channel 23, and a distal opening 211 in fluidic communication with the connecting element 10 to a medical device. The distal opening 211 is located close to a distal wall 212 of the blocking chamber 21, of generally truncated or annular shape. This distal wall 212 is adapted to receive the sleeve 24 and block it in translation, without obstructing the distal opening 211.

The base 2 can also comprise a transparent viewing chamber 26, extending between the blocking chamber 21 and the connecting element 10. This viewing chamber 26 is made of transparent material or can comprise a viewing window made of transparent material, to allow an operator to see the contents of the viewing chamber 26. The viewing chamber 26 is connected to the blocking chamber 21 by means of the distal wall 212. It can especially have a tubular form, whereof the dimensions correspond substantially to the diameter of the distal opening 211 of the blocking chamber 21.

As will be seen below, the viewing chamber 26 is adapted to receive a free end of the catheter 4 and play the role of visual marker for positioning the catheter 4 in the base 2.

The viewing chamber 26 can also enable connection of the shell 3 on the base 2 to close the releasable blocking system 1. The hooking means 32 of the shell 3 are provided opposite the viewing chamber 26. In particular, the hooking means 32 can comprise two tabs 321 adapted to be placed on either side of the chamber 26 when the shell 3 is folded back on the base 2, and having at the level of their free end hooks 322 opposite adapted to engage with the viewing chamber 26. The tabs 321 are configured to spread apart to slide on the lateral walls of the viewing chamber 26 until the hooks 322 engage under the viewing chamber 26, where they are held in position under the effect of the elastic return of the tabs, keeping the shell 3 fixed on the base 2. Optionally, this elastic return can especially serve as auditory marker for the operator verify that the system 1 is correctly closed.

To open the system 1, it is enough to dislodge the hooks 322 to be able to separate the shell 3 from the base 2. For this, an orifice 273 can be made in a lower surface 274 of the base 27 of the base 2, opposite the viewing chamber 26, to allow passage of the nozzle of an object, such as a syringe nozzle, while the hooks 322 can have a lower inclined surface 323 acting as ramp. It suffices for the operator to introduce the object in the orifice 273 so as to press on the lower surfaces 323 of the hooks 322, to spread the hooks 322 and to release the viewing chamber 26.

Figure 6:
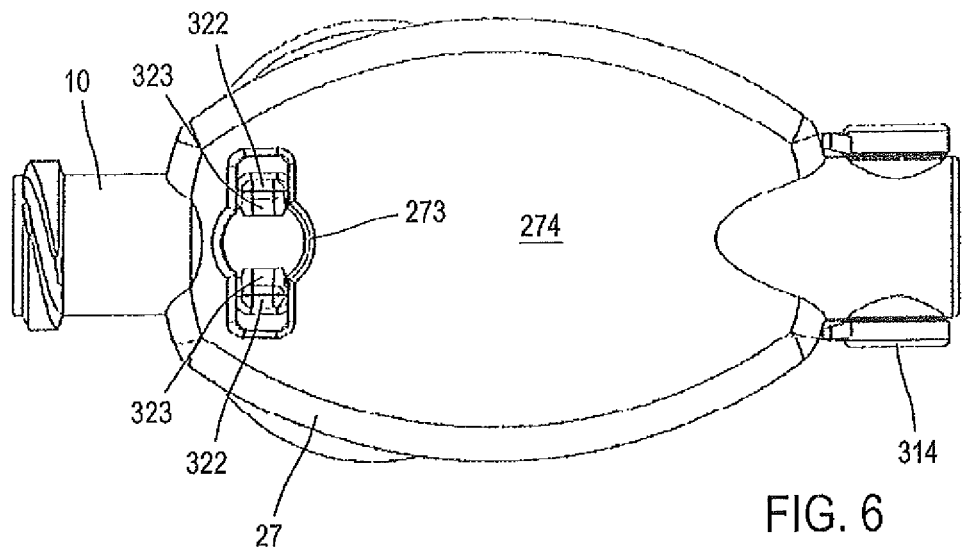
Figure 7:
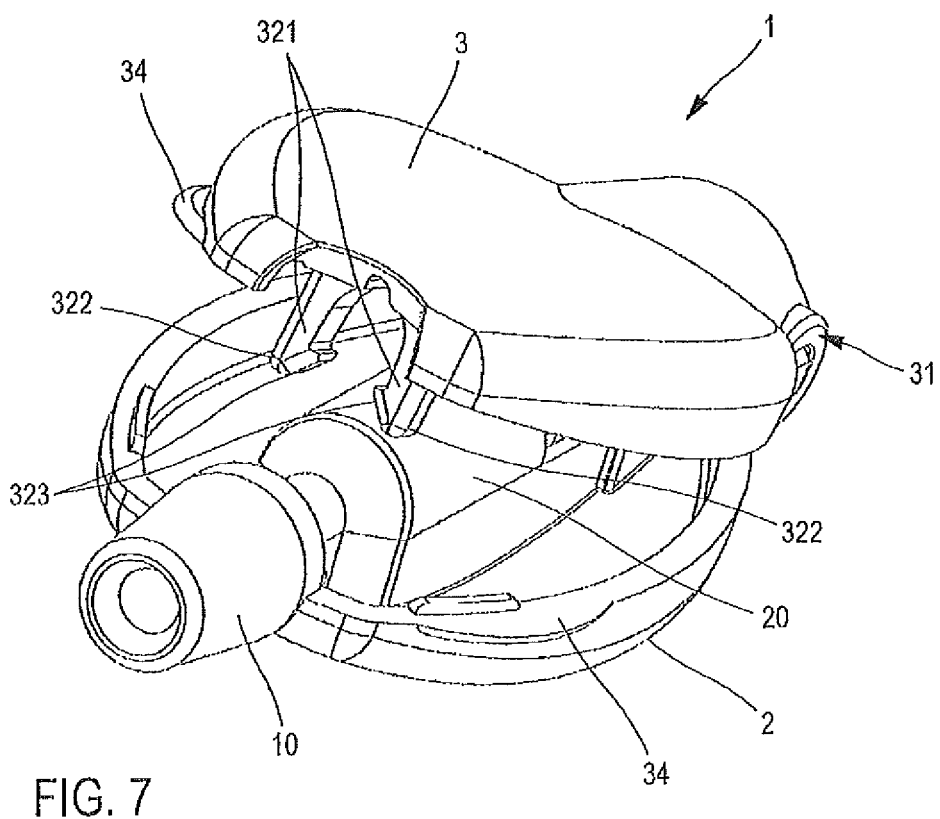
FIG. 7 is a view in perspective of an embodiment of a releasable blocking system according to the invention, in open position.
Figure 8A:
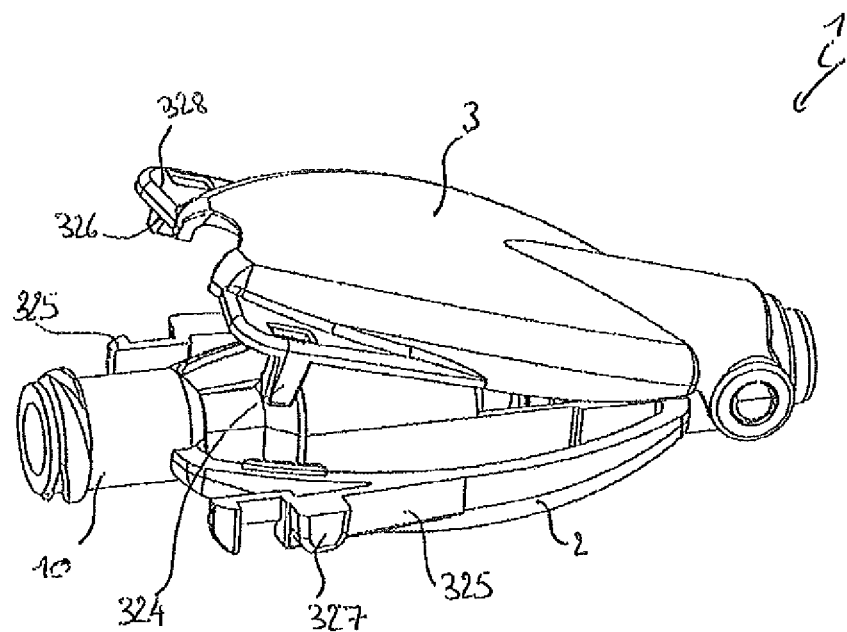
FIG. 8a is a view in perspective of another embodiment of a releasable blocking system according to the invention, in open position.
Figure 8B:
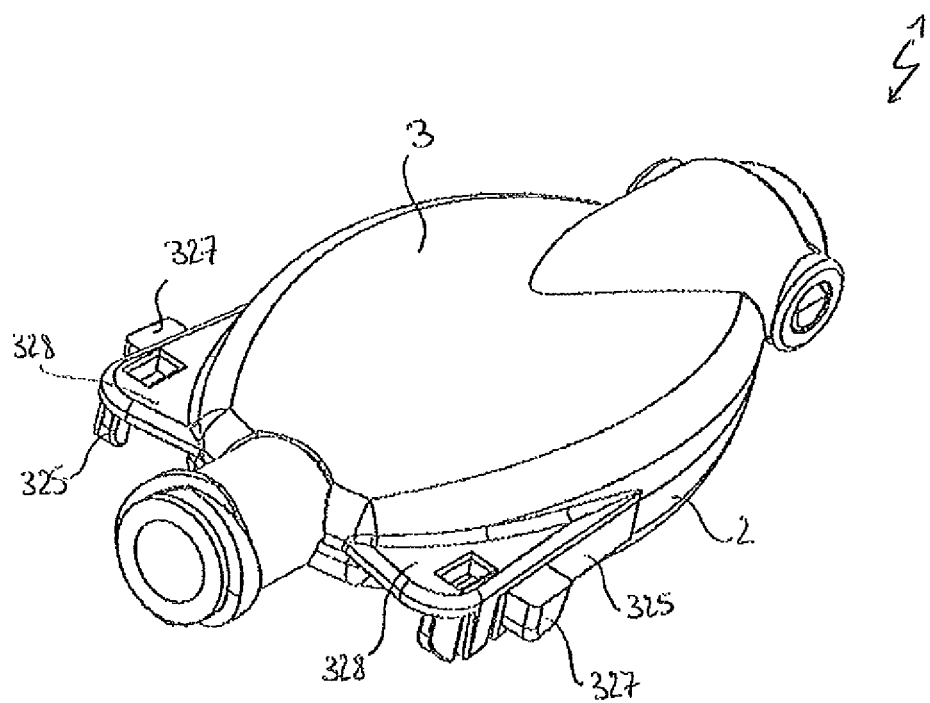
FIG. 8b is a view in perspective of the embodiment of FIG. 8a, in closed position.
Figure 8C:
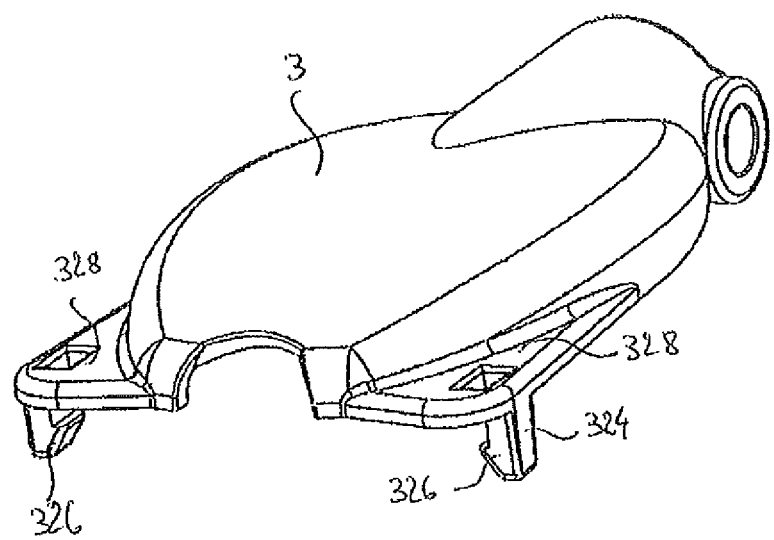
Figure 8D:
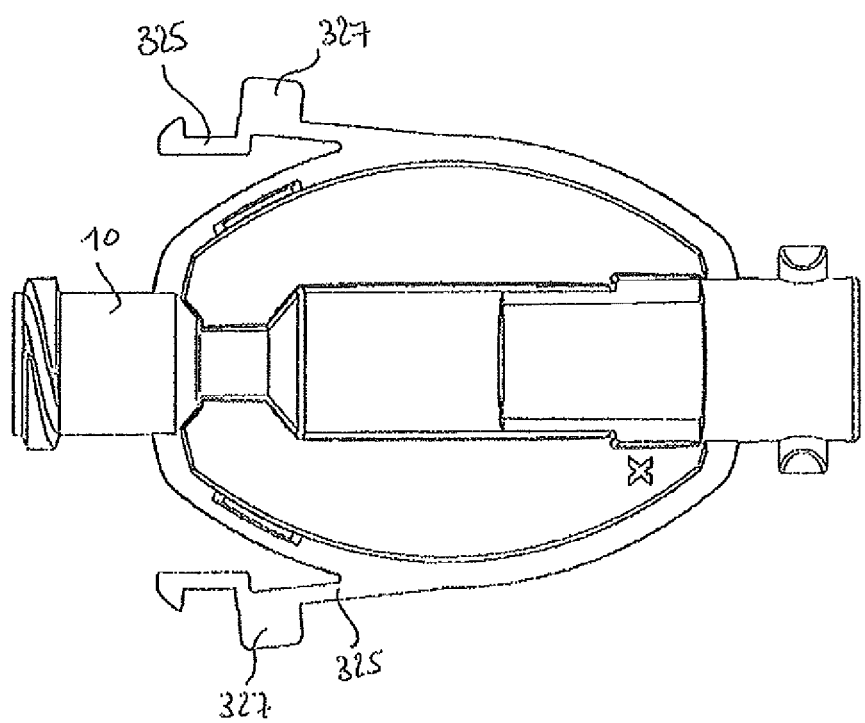

The orifice 273 can be dimensioned so as to leave a passage for the nozzle of the object. As a variant, the hooks 322 can brush the level of the lower surface 274 of the base via the orifice 273, as illustrated in FIG. 6. The orifice 273 is dimensioned so as to allow introduction of the nozzle of the object and the spread of the hooks 322.

As a variant, as illustrated in FIGS. 8a to 8d, the hooking means 32 of the shell 3 can be provided on either side of the shell 3 and of the base 2. In particular, the hooking means 32 can comprise two lateral tabs 324 extending in the direction of the base 2 when the shell 3 is folded back on the base 2, and having at the level of their free end hooks 326 opposite regard adapted to engage with snap-locking 325 tabs, extending from the base 2.

The snap-locking tabs 325 of the base 2 are fixed on the base 2, along its lateral sides, and extend substantially parallel to the longitudinal axis X in the direction of the connector 10. Preferably, the snap-locking tabs 325 are dimensioned so as not to exceed the upper surface of the base 2. The snap-locking tabs 325 are deformable elastically, so as to allow passage of the hooks 326 and to keep them in position. So, the lateral tabs 324 are provided to spread apart to slide on the snap-locking tabs 325 until the hooks 326 engage under the snap-locking tabs 325 where they are held in position under the effect of the elastic return of the snap-locking tabs 325, keeping the shell 3 fixed to the base 2. Optionally, this elastic return can especially serve as auditory marker for the operator to verify that the system 1 is correctly closed.

In the embodiment illustrated in the figures, the lateral tabs 324 are fixed on a surface 328 extending in the plane of the lower surface of the shell 3 so as to be offset relative to the external sides of said shell 3. In this way, during closing of the shell 3 on the base 2, the hooks 326 come into contact with the external surface of the snap-locking tabs 325, to deform it by bringing it closer to the base 2 until said hooks 326 can pass through.

The snap-locking tabs 325 are also each fitted with a protuberance 327, formed on their external surface so as to be accessible by the operator, to allow the operator to deform the snap-locking tabs 325 by simple finger pressure by bringing it closer to the base 2, and therefore to release the hooks 326. Using voluntary movement, the operator can separate the shell 3 from the base 2 and open the releasable blocking system 1 to release the catheter.

Advantageously, the snap-locking of the tabs 324 and 325 constitutes an auditory marker for the operator, allowing him to ensure proper closing of the releasable blocking system. Also, the hooking means 32 ensure snap-locking security, where intervention by the operator for its reopening is needed.

Optionally, the shell 3 and/or the base 2 can be fitted with reliefs 34, for example lugs, for easier handling of the system 1 to lift the shell 3.

The sleeve 24 is preferably made of deformable material, and can be compressible. For example, the sleeve 24 can be made of elastomer material, such as polyisoprene.

The sleeve 24 comprises a blocking aperture 241 designed to receive the catheter 4. The internal diameter of this blocking aperture 241 is selected to be substantially equal to that of the catheter 4, to allow its introduction in the aperture 241 and than make its blockage easier when the sleeve 24 is deformed by the actuator 25. The blocking aperture 241 is preferably coaxial to the sleeve 24.

The form of the sleeve 24 is substantially complementary to the form of the internal space of the blocking chamber 21 to ensure its positioning in the blocking chamber 21 and therefore the positioning of the blocking aperture 241 which is designed to block the catheter 4. So, for a blocking chamber 21 of substantially tubular form, the sleeve 24 is substantially cylindrical in revolution in shape. Its diameter is also selected as a function of the internal diameter of the blocking chamber 21, to allow its insertion in the blocking chamber 21 and ensure its positioning relative to the housing 20. For example, the external diameter of the sleeve 24 can be substantially equal to the internal diameter of the blocking chamber 21.

So, once the sleeve 24 is positioned in the blocking chamber 21, the blocking aperture 241 is coaxial to the blocking chamber 21 (and to the housing 20).

The ring 22 can also have an substantially tubular form, and comprise a proximal opening and a distal opening terminating in the channel 23. In the embodiment illustrated in the figures, the ring 22 bears the connection means to the shell 3, here the two pins 271 extending radially relative to the longitudinal axis X, in the plane of the base 2. The shell 3 comprises the two lugs 311, adapted to be mounted on the pins 271, allowing the shell 3 to pivot about the axis of the pins 271. The form of the shell 3 is also selected so as not to prevent introduction of the catheter 4 when the blocking system 1 is open, that is, when the shell 3 is not folded back on the base 2. For example, the shell 3 can be formed such that its proximal end is stopped against the wall external of the ring 22 when the blocking system 1 is open.

The channel 23 comprises an opening extending opposite the shell 3 of the blocking system 1. For example, the channel 23 can have a U-shaped wall 232, of semi-circular cross-section, in the extension of the ring 22, the opening 231 extending over its entire length. As a variant the channel 23 can be of tubular form, the opening 231 being made in the form of a window of appropriate dimensions to receive the drive element 33 of the shell 3.

The actuator 25 is adapted to come into contact with the sleeve 24 and push it in the direction of the distal wall 212 of the housing 20 to reduce the internal section of the blocking aperture 241 and block the catheter 4 in a position relative to the base 2.

For this purpose, the actuator 25 is mobile in translation along the longitudinal axis X, and has a proximal guide part 252, housed at least partially in the ring 22, and a distal part 254 forming a pusher, housed at least partially in the channel 23.

Its distal part 254 is adapted to push the sleeve 24, while its proximal part 252, which acts as guide, positions the catheter 4 relative to the sleeve 24 and to the base 2, and the actuator 25 in the blocking chamber 21.

The actuator 25 comprises a guide aperture 251 passing through the catheter 4, whereof the proximal end 253 can be widened out for easy introduction of the catheter 4. The internal diameter of this guide aperture 251 is selected so as to be slightly larger than that of the catheter 4, to allow introduction of the catheter 4 in the aperture 251 and then make its guiding to the sleeve 24 easier. For example, the diameter of the guide aperture 251 can be decreasing between its widened proximal end 253 and its distal end, arranged opposite the blocking aperture 241 of the sleeve. According to an embodiment, the diameter of the distal end of the guide aperture 251 is at most equal to the diameter of the proximal end of the blocking aperture 241, to prevent the catheter 4 form stopping against the sleeve 24 during its introduction.

The guide aperture 251 is preferably coaxial to the actuator 25. Therefore, once the sleeve 24 is positioned in the ring 22, the guide aperture 251 is coaxial to the ring 22 (and therefore to the housing 20).

The form of the proximal guide part 252 of the actuator 25 is preferably substantially complementary to that of the ring 22, which ensures alignment of the actuator 25 with the channel 23 and the blocking chamber 21. Therefore, for a ring 22 of substantially tubular form, the guide part 252 is of substantially cylindrical in revolution form. The diameter of the guide part 252 is also as a function of the internal diameter of the ring 22, so as to allow insertion of the guide in the ring 22, and for it to be held in the direction of translation of the actuator 25.

The proximal guide part 252 can also comprise means 258 provided to prevent the actuator 25 from coming out of the system 1. These means 258 can especially be one or more protuberances projecting from the external surface of the proximal part 252, at a distance from its proximal end. The dimensions of the protuberance 258 are selected such that the external diameter of the proximal part 252 at the level of the protuberance 258 is greater than the internal diameter of the ring 22. In this way, once the actuator 25 is in place in the blocking system 1, the latter cannot be extracted from the housing 20 to the extent where the protuberance 258 prevents it being moved beyond a certain point in the direction of the proximal end of the ring 22.

Optionally, the axial position of the protuberance 258 can also be selected so as to ensure that a piston 257 of the actuator 25, as will be described later, is always in contact with the sleeve 24, that the actuator 25 is in the rest position in which it does not axially deform the sleeve 24, or in the blocking position, in which the actuator 25 is introduced in the blocking chamber 21 to deform the sleeve 24. This in fact ensures the continuity of the guide 251 and blockage 241 apertures, even in the rest position of the actuator 25, and therefore makes introduction of a catheter 4 easier.

The distal part 254 extends substantially in the channel 23, and comprises a body 256, the abovementioned piston 257 and the drive element 255. The body 256, the piston 257 and the drive element 255 can especially be monobloc. As a variant, the piston 257 and the drive element 255 can be attached to the body 256.

The body 256 extends along the longitudinal axis X, between the proximal guide part 252 of the actuator 25 and the distal end of the actuator 25, and connects the piston 257 to the drive element 255. The diameter of the body 256 can especially be less than the internal diameter of the ring 22 and/or of the blocking chamber 21.

The piston 257 is arranged at the level of the distal end of the distal part 254. It has the form of a cylindrical head, extending transversally relative to the longitudinal axis X, and has a substantially plane distal wall 257a extending transversally to the direction of translation of the actuator 25. The head can for example be cylindrical in revolution, and have sufficient thickness to be capable of deforming the sleeve 24 and blocking a catheter 4, as illustrated in FIGS. 5b, 5c, 6b and 6c. As a variant, the head can be conical and have a diameter decreasing between the distal wall 257a of the piston 257 and the body 256.

The drive element 255 extends between the piston 257 and the proximal guide part 252, and is arranged so as to be arranged at least partially opposite the opening 231 of the channel 23. The drive element 255 is adapted to cooperate with the drive element 33 complementary to the shell 3. The form of the drive elements 255, 33 is determined such that the closing of the shell 3 on the base 2 causes the translation of the actuator 25 in the direction of the sleeve 24 over a determined distance.

For example, the drive element 255 of the base 2 has a proximal return ramp 255a for forces engendering a thrust force in the direction of the sleeve 24 when a force is applied to said element 255 in a direction normal to the direction of translation. For this, the return ramp 255 extends substantially transversally to the body 256 of the distal part 254, and the ramp is oriented obliquely at an angle preferably between 15° and 85° with the longitudinal axis X. The angle of the return ramp 255a is determined as a function of the distance to cover by the actuator 25 to axially compress the sleeve 24, and depends on the diameter of the element 255. Therefore, the smaller the angle, the bigger the diameter of the element 255 should be for the same distance to cover.

The thrust force is applied by the drive element 33 of the shell 3. For this, the drive element 33 of the shell 3 has the form of a projecting part, adapted to cooperate with the return ramp 255a to shift the actuator 25. It is arranged in the shell 3 so as to come into contact with the element 255 when the shell 3 is folded back on the base 2 to close the blocking system 1, for example by rotation of the shell 3 relative to the axis of the pins 271, then to rest on the return ramp 255a. As the actuator 25 is mobile in translation in the housing 20, it is displaced in the housing 20 in the direction of the sleeve 24 while the projection progresses on the ramp 255a, until the shell 3 is stopped against the base 2

In the embodiment illustrated in the figures, the drive element 255 has an annular extending form about the body 256 of the distal part 254 in the direction of the shell 3, whereof the external diameter is substantially equal to that of the sleeve 24, and whereof the return ramp 255a extends on either side of the body 256. The shell 3 can have two projections 33, each being adapted to come into contact with the return ramp 255a.

The shell 3 can be locked in this position by means of the hooking means 32.

Optionally, the shell 3 can also be held in position by cooperation of the element 255 with the projection 33. For this, the element 255 has, in the extension of the ramp 255a, in the direction of the base 27 of the base 2, a locking wall 255b extending transversally to the longitudinal axis X. In this way, after having travelled the inclined return ramp 255a, the projection 33 is stopped against the locking wall 255b of the element 255, which locks the system 1 in the closed position. In effect, given that the sleeve 24 is deformed by the actuator 25 when the system 1 is closed, it applies an axial force to the piston 257 in the direction of the proximal end of the blocking system 1 to regain its initial form, which presses the locking wall 255b against the projection 33. The locking can be improved with use of a projection 33 whereof the distal wall 33b is parallel to the locking wall 255b of the element 255 (when the blocking system 1 is closed), such that the locking wall 255b and the distal wall 33b are in contact over their entire surface, according to a plane perpendicular to the direction of the effort applied by the sleeve 24 (axial direction, parallel to the longitudinal axis X). If needed, the distal wall 33b of the projection 33 can also have an inclined part 33a complementary to the return ramp 255a, such that when the system is closed, the distal wall 33b is en contact both with the locking wall 255b and the return ramp 255a, to reinforce blockage of the shell 3 on the base 2.

By way of advantage, the blockage of the shell 3 by cooperation of the locking wall 255b of the element 255 with the projection 33 creates added resistance during unlocking of the hooks 322.

As a variant, and by way of equivalent, the actuator can bear the projection and the shell 3 the element with return ramp. The operation of the blocking system 1 remains the same, the closing of the system 1 causing displacement of the actuator 25 in the housing due to the sliding of the projection (forming the drive element 255) on the drive wall of the cam (forming the drive element 33 of the shell).

To make introduction of a catheter 4 in the guide aperture 251 easier, the length of the guide part 252 can be greater than the length of the ring 22, along the longitudinal axis X. In this way, when the proximal guide part 252 is stopped against the protuberance 258, its proximal end 253 projects beyond the ring 22 and the base 2, disengaging the widening of the guide aperture 251. This embodiment also has the advantage of allowing an operator to verify that the blocking system 1 is not engaged and the sleeve 24 is not compressed, the actuator 25 being clearly in its rest position.

Also, to prevent actuator 25 from turning on itself, either about the longitudinal axis X, which could have as consequence that the element 255 is no longer opposite the projection 33 and would prevent blockage of the catheter 4, the actuator 25 and the housing can be fitted with one or more grooves and rectilinear throats, extending parallel to the longitudinal axis X. For example, the ring 22 can comprise four throats 221 distributed equidistantly over its internal surface, cooperating with as many grooves 250 projecting from the proximal guide part 252 of the actuator, or vice versa.

As a variant, the grooves 221, can extend from the distal part 252 of the actuator 25, for example at the level of the piston 257, and cooperate with rectilinear throats 250 made in the blocking chamber 21 of the housing 20 (or vice versa). In this variant embodiment, the protuberance 258 is positioned on the actuator 25 so as to ensure that the piston 257 of the actuator 25 stays in the blocking chamber 21 in its rest position as in its blocking position.

An operator can therefore connect a catheter 4, even one of very small diameter, simply, ergonomically, safely, rapidly and with minimal effort, because of a releasable blocking system 1 according to the invention.

For this, he first opens the blocking system 1, by pulling the shell 3 away from the base 2 by rotation of the shell 3 about the axis of the pins 271. The actuator 25 exerts no effort on the sleeve 24, whereof the blocking aperture 241 is consequently open to allow introduction of the catheter 4, and its proximal end 253 projects if needed beyond the ring 22. He then introduces the catheter 4 in the guide aperture 251 of the actuator 25, then pushes on the catheter 4 to have it successively pass through the actuator 25 and the sleeve 24, until it reaches the viewing chamber 26. Because of the viewing chamber 26, the operator can verify visually that the distal end of the catheter 4 is sufficiently near the connecting element 10. The catheter 4 is ready to be blocked detachably by the blocking system 1, and extends through the aperture 251 of the actuator 25, the aperture 241 of the sleeve 24, and into the viewing chamber 26.

The operator can then fold back the shell 3 onto the base 2, to close the blocking system 1 and block the catheter 4. During closing, the projection 33 of the shell 3 abuts against the cam 255 of the actuator 25. When closing is continued despite this initial resistance, the actuator 25 is displaced in the direction of the sleeve 24 which it deforms axially (the sleeve 24 being held by the distal wall 212 of the blocking chamber 21). The effect of this axial deformation, along the longitudinal axis X of the base 2, is to reduce the cross-section of the blocking aperture 241 of the sleeve 24, and block the catheter 4 in position in said sleeve 24.

The operator can fix a medical device, for example a filter, by screwing an adapted nozzle onto the connector 10 of the system 1.

When the operator wants to withdraw the catheter 4, all he needs to do is disconnect the medical device from the connector 10, then open the blocking system 1, inserting a object of appropriate dimensions in the orifice 273 of the base 2, then move the shell 3 away from the base by rotation about the pins 271 of the base 2 to disengage the blocking elements 255 and 33 and return the actuator 25 to its rest position. The sleeve 24 can resume its initial form and release the catheter 4, allowing the operator to extract the catheter from the blocking system 1.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A releasable blocking system of a catheter, comprising a base adapted to receive a catheter, and a shell, rotatably mounted on the base between an open position, in which the shell is away from the base, and a closed position, in which the shell is hooked on the base and blocks the catheter in position, wherein:
   the base defines a housing having a principal direction according to a longitudinal axis, said housing enclosing a sleeve provided with a blocking aperture extending along the longitudinal axis and adapted to abut against a distal wall of the housing, wherein the housing comprises successively, along the longitudinal axis, a blocking chamber and a ring, a channel extending between the blocking chamber and the ring,
   the system comprises an actuator provided with a guide aperture extending along the longitudinal axis and mobile in translation along the longitudinal axis in the housing between a rest position and a blocking position in which the actuator applies an axial force to the sleeve to deform it, the actuator comprising a first drive element,
   the blocking aperture and the guide aperture are adapted to receive a catheter,
   the shell comprises a second drive element, adapted to cooperate with the first drive element of the actuator when the shell is shifted from its open position to its closed position, and shift the actuator along the longitudinal direction to its blocking position, and
   wherein the first drive element of the actuator has a return ramp extending outwardly from a distal part of the actuator and protruding between the blocking chamber and the ring of the housing through the channel, and the second drive element comprises a projecting part extending from the shell, arranged so as to penetrate the channel of the housing and come into contact with said return ramp when the shell is brought to its closed position.

2. The releasable blocking system as claimed in claim 1, in which an external diameter of the distal part of the actuator is at most equal to an internal diameter of the ring.

3. The releasable blocking system as claimed in claim 1, in which an internal diameter of the blocking aperture of the sleeve is substantially equal to an external diameter of the catheter.

4. The releasable blocking system as claimed in claim 1, in which the channel comprises an opening extending opposite the first drive element of the actuator, the second drive element of the shell being positioned so as to cooperate with the first drive element through said opening of the channel.

5. The releasable blocking system as claimed in claim 1, in which the first drive element is substantially annular in form, and the return ramp is oriented obliquely relative to a plane normal to the longitudinal direction.

6. The releasable blocking system as claimed in claim 5, in which the first drive element also comprises a proximal locking wall extending from the return ramp in a plane substantially perpendicular to the longitudinal direction, adapted to come into contact with a distal wall of the projecting part of the second drive element when the shell is in its closed position.

7. The releasable blocking system as claimed in claim 1, in which the distal part of the actuator also comprises a protuberance extending radially from said distal part, adapted to prevent the actuator from coming out of the housing.

8. The releasable blocking system as claimed in claim 1, in which the actuator and the housing are fitted with one or more rectilinear grooves and throats, extending radially from the actuator, adapted to prevent a rotation of the actuator in the base.

9. The releasable blocking system as claimed in claim 1, in which the base further comprises a connecting element to a medical device, said connecting element being in fluidic communication with the housing.

10. The releasable blocking system as claimed in claim 9, also comprising a transparent viewing chamber extending between the housing and the connecting element, adapted to receive a free end of the catheter.

11. The releasable blocking system as claimed in claim 10, in which the shell comprises hooking means on the base.

12. The releasable blocking system as claimed in claim 11, in which the hooking means comprise at least one hook engaged in an orifice in the base so as to be released to open the releasable blocking system.

13. The releasable blocking system as claimed in claim 11, in which the hooking means comprise hooks, fixed on the shell and adapted to cooperate by snap-locking with tabs, extending from the base, said tabs being elastically deformable so as to allow an operator to release the hooks by simple pressure.

14. A releasable blocking system of a catheter, comprising a base adapted to receive a catheter, and a shell, rotatably mounted on the base between an open position, in which the shell is away from the base, and a closed position, in which the shell is hooked on the base and blocks the catheter in position, wherein:
   the base defines a housing having a principal direction according to a longitudinal axis, said housing enclosing a sleeve provided with a blocking aperture extending along the longitudinal axis and adapted to abut against a distal wall of the housing, wherein the blocking aperture is a cylinder of revolution, and wherein the housing comprises successively, along the longitudinal axis, a blocking chamber and a ring, a channel extending between the blocking chamber and the ring,
   the system comprises an actuator provided with a guide aperture extending along the longitudinal axis and mobile in translation along the longitudinal axis in the housing between a rest position and a blocking position in which the actuator applies an axial force to the sleeve to deform it, the actuator comprising a first drive element, the blocking aperture and the guide aperture are adapted to receive a catheter, and the shell comprises a second drive element, adapted to cooperate with the first drive element of the actuator when the shell is shifted from its open position to its closed position, and shift the actuator along the longitudinal direction to its blocking position.

15. The releasable blocking system as claimed in claim 14, in which an external diameter of a distal part of the actuator is at most equal to an internal diameter of the ring.

16. The releasable blocking system as claimed in claim 14, in which an internal diameter of the blocking aperture of the sleeve is substantially equal to an external diameter of the catheter.

17. The releasable blocking system as claimed in claim 14, in which the housing comprises an opening extending opposite the first drive element of the actuator, the second drive element of the shell being positioned so as to cooperate with the first drive element through said opening of the housing.

18. The releasable blocking system as claimed in claim 14, in which the first drive element of the actuator has a return ramp extending outwardly from a distal part of the actuator and protruding between the blocking chamber and the ring of the housing through the channel, and the second drive element comprises a projecting part extending from the shell, arranged so as to penetrate the channel of the housing and come into contact with said return ramp when the shell is brought to its closed position.

* * * * *